(12) United States Patent
Barnsley

(10) Patent No.: US 12,334,217 B2
(45) Date of Patent: Jun. 17, 2025

(54) SYSTEMS AND METHODS FOR CUSTOMIZING SERVICES TO USERS

(71) Applicant: CriticalArc Pty, Sutherland (AU)

(72) Inventor: Dominic Barnsley, Miranda (AU)

(73) Assignee: CriticalArc Pty, Sutherland (AU)

( * ) Notice: Subject to any disclaimer, the term of this patent is extended or adjusted under 35 U.S.C. 154(b) by 0 days.

(21) Appl. No.: 18/223,036

(22) Filed: Jul. 18, 2023

(65) Prior Publication Data

US 2025/0029719 A1 Jan. 23, 2025

(51) Int. Cl.
| | | |
|---|---|---|
| G06F 3/0481 | (2022.01) | |
| G16H 10/60 | (2018.01) | |
| G16H 40/67 | (2018.01) | |

(52) U.S. Cl.
CPC ........... G16H 40/67 (2018.01); G06F 3/0481 (2013.01); G16H 10/60 (2018.01)

(58) Field of Classification Search
CPC ...... G06F 3/0484; G06F 16/739; G06F 40/40; G06F 13/122; G06F 13/126; G06F 13/4221; G06F 16/285; G06F 16/434; G06F 16/583; G06F 21/32; G06F 21/554; G06F 21/572; G06F 3/017; G06F 3/167; G06F 40/58; G06F 8/65; G06F 11/3688; G06F 11/3692; G06F 15/177; G06F 16/29; G06F 16/958; G06F 3/04817; G06F 1/163; G06F 11/008; G06F 11/24; G06F 21/31; G06F 21/629; G06F 21/36; G06F 21/62; G06F 21/70; G06F 2221/032; G06F 2221/2105; G06F 3/048; G06F 3/0486; G06F 3/0488; G06F 3/16; G06F 2221/2149; G06F 21/6218; G06F 16/9535; G06F 16/951; G06F 21/46; G06F 21/6245; G06F 16/22; G06F 21/6254; G06F 16/90332; G06F 16/9035; G06F 16/9566; G06F 3/0482; G06F 40/30; G06F 40/35; G06F 16/2228; G06F 16/3322; G06F 16/338; G06F 16/748; G06F 16/9538; G06F 16/9554; G06F 17/40; G06F 21/53; G06F 21/552; G06F 21/6281; G06F 2221/2101; G06F 2221/2129;

(Continued)

(56) References Cited

U.S. PATENT DOCUMENTS

| | | | | |
|---|---|---|---|---|
| 2015/0180746 A1* | 6/2015 | Day, II | .................... | H04L 67/55 |
| | | | | 455/405 |
| 2017/0228127 A1* | 8/2017 | Mukherjee | .............. | G06F 9/546 |
| 2018/0084100 A1* | 3/2018 | Chockalingam | ..... | H04M 3/5116 |

(Continued)

*Primary Examiner* — Rayeez R Chowdhury
(74) *Attorney, Agent, or Firm* — Emanus, LLC; Willie Jacques

(57) ABSTRACT

A method for customizing a service is disclosed. The method includes receiving communication from a user communication device responsive to activation of a graphical user interface (GUI) component. Further, the method includes determining, responsive to receiving the communication, by the one or more servers, contextual information based at least on date and time of activating the GUI component, information of a user associated with the user communication device, and a location of the user communication device. The method also includes generating at least one contextual GUI element based on the contextual information and communicating the at least one contextual GUI element to the user communication device.

20 Claims, 4 Drawing Sheets

(58) Field of Classification Search
CPC ............. G06F 3/04842; G06F 3/04847; G06F 3/04883; G06F 30/12; G06F 30/13
See application file for complete search history.

(56) References Cited

U.S. PATENT DOCUMENTS

2020/0059776 A1* 2/2020 Martin ............... H04M 1/72439
2021/0297461 A1* 9/2021 Athwal .................. G06Q 20/22

* cited by examiner

SYSTEMS AND METHODS FOR CUSTOMIZING SERVICES TO USERS

TECHNICAL FIELD

The present disclosure is related to healthcare services, and more particularly related to systems and methods for providing healthcare services to users.

BACKGROUND

The subject matter discussed in this background section should not be assumed to be prior art merely because of its mention herein. Similarly, any problems mentioned in this background section or associated with the subject matter of this background section should not be assumed to have been previously recognized in the prior art. The subject matter as disclosed in this background section merely represents different approaches related to providing healthcare services to users, wherein such services themselves may also correspond to implementations of the claimed technology and invention.

An emergency is a sudden unforeseen situation that requires immediate response and help by concerned agencies such as, but not limited to, police, ambulance, fire brigade, civil defense, or disaster management. Currently, different emergency communication and response systems are in place for these agencies. The emergency communication and response systems are accessed through different contact numbers. In addition, a number of private hospitals have also set up their separate helpline numbers for medical emergencies. During an emergency, location information is provided by a caller, and the emergency communication and response system rely on the location information provided by a caller. In this scenario, if the caller is either not able to convey his or her location, or the location conveyed by the caller is vague or inaccurate, there is a possibility that his or her request for help is handed over to an agency that may not be in the immediate vicinity of the caller, thereby resulting in loss of crucial time in providing response to the caller.

Further, there are different contact numbers for different emergency services. The caller needs to dial the relevant number depending on the type of emergency situation. In case the caller does not know the correct emergency number to dial, the caller may be deprived of any help or may get the help after a substantial delay. Also, there may be a situation where multiple agencies need to be contacted. For example, a car accident may result in fire, and occupants of the car may suffer burn injuries. Such a situation would require calling a fire brigade as well as an ambulance. Getting the right contact numbers and explaining the same situation to each of them may result in a delay in a situation where one would want an instant response. Further, communications with these agencies are typically limited to audio calls with narrow functionality since most emergency service providers that receive emergency calls currently lack the capacity for more appropriate communications.

Prior arts, for various aspects contained there within, relevant to this disclosure include U.S. patent application Ser. No. 20200135005A1 to Katz et. al., JP patent application No. 2009216445A to Shuichi et. al. In each of the prior arts, a notification and navigational systems are disclosed for aiding a user in an emergency situation. However, the prior arts do not provide an end to end solution for the user facing the emergency in different situations such as medical, security etc.

In particular, reference '005 to Katz describes systems, devices, methods, and media for connecting a user for providing emergency assistance based on emergency alerts from triggering devices such as voice or sound triggered emergency alerts. In some cases, the location of the emergency is provided. However, unlike the subject matter of the disclosed invention, the prior art does not disclose about providing elements such as hyperlinks to a required website based on the emergency situation of the user, emergency contact numbers to the user, related email address for contact to the user, list and contact details of law inforcement offices, hospitals etc.

In particular, reference '445 to Shuichi describes highly convenient emergency navigation terminal capable of conveying a patient to a hospital in a shorter time and of being utilized even when a disease is not advanced to the extent that an ambulance should be called. However, unlike the subject matter of the disclosed invention, the prior art does not disclose about fetching of contextual information related to current health of a user. Further, the prior art does not disclose about providing elements such as hyperlinks to a required website based on the emergency situation of the user, emergency contact numbers to the user, related email address for contact to the user, list and contact details of law inforcement offices, hospitals etc.

Accordingly, there is a need for improved systems and methods that overcome above mentioned disadvantages.

SUMMARY

The present disclosure is directed to systems and methods for providing healthcare services to users.

In an exemplary embodiment, a method for customizing healthcare services for users is disclosed. The method includes receiving, by one or more servers, communication from a user communication device responsive to activation of a graphical user interface (GUI) component. The GUI component enables a user to establish instant communication with the one or more servers during an emergency situation. Further, the method includes, determining, responsive to receiving the communication, by the one or more servers, contextual information based at least on date and time of activating the GUI component, information of a user associated with the user communication device, and a location (i.e., a current location) of the user communication device. The contextual information based at least on the date and time of activating the GUI component, information of the user associated with the user communication device, and the location of the user communication device, allows the user communication device to provide customized assistance to the user as per the requirement. The method also includes generating, by the one or more servers, at least one contextual GUI element based on the contextual information, and communicating, by the one or more servers, the at least one contextual GUI element to the user communication device. The at least one contextual GUI element provides a one stop solution for the user to ask for assistance from the at least one contextual GUI element. The at least one contextual GUI element provides links of multiple services. The links are contextual and may be determined according to who is requesting assistance, from where the request is being required, and at what time the user is requesting the assistance.

In another exemplary embodiment, a system for customizing healthcare services for users is disclosed. The system includes a user communication device configured to transmit a communication responsive to activation of a GUI component. The GUI component enables a user to establish instant communication with one or more servers during an emergency situation. The system further includes one or more servers configured to receive the communication from the user communication device. The one or more servers are further configured to, responsive to receiving the communication, determine contextual information based at least on date and time of activating the GUI component, information of a user associated with the user communication device, and a location (i.e., a current location) of the user communication device. The contextual information based at least on the date and time of activating the GUI component, information of the user associated with the user communication device, and the location of the user communication device, allows the user communication device to provide customized assistance to the user as per the requirement.

Also, the one or more servers are configured to generate at least one contextual GUI element based on the contextual information, and communicate the at least one contextual GUI element to the user communication device. The at least one contextual GUI element provides a one stop solution for the user to ask for assistance from the at least one contextual GUI element. The at least one contextual GUI element provides links of multiple services. The links are contextual and may be determined according to who is requesting assistance, from where the request is being required, and at what time the user is requesting the assistance.

In yet another exemplary embodiment, a computer program product is disclosed. The computer program product comprises instructions which, when the program is executed by a computing device having a memory and a processor coupled to the memory, causes the computing device to receive communication from a user communication device responsive to activation of a GUI component, responsive to receiving the communication, determine contextual information based at least on date and time of activating the GUI component, obtain and process information of a user associated with the user communication device, determine a location (i.e., a current location) of the user communication device, generate at least one contextual GUI element based on the contextual information, and communicate the at least one contextual GUI element to the user communication device.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

The accompanying drawings illustrate various embodiments of systems, methods, and embodiments of various aspects of the disclosure. Any person of ordinary skill in the art will appreciate that the illustrated element boundaries (e.g., boxes, groups of boxes, or other shapes) in the figures represent one example of the various boundaries representative of the disclosed invention. It may be that in some examples one element may be designed as multiple elements or that multiple elements may be designed as one element. In other examples, an element shown as an internal component of one element may be implemented as an external component in another and vice versa. Furthermore, elements may not be drawn to scale. Non-limiting and non-exhaustive descriptions of the present disclosure are described with reference to the following drawings. The components in the figures are not necessarily to scale, emphasis instead being placed upon the illustrated principles.

Figure 1:
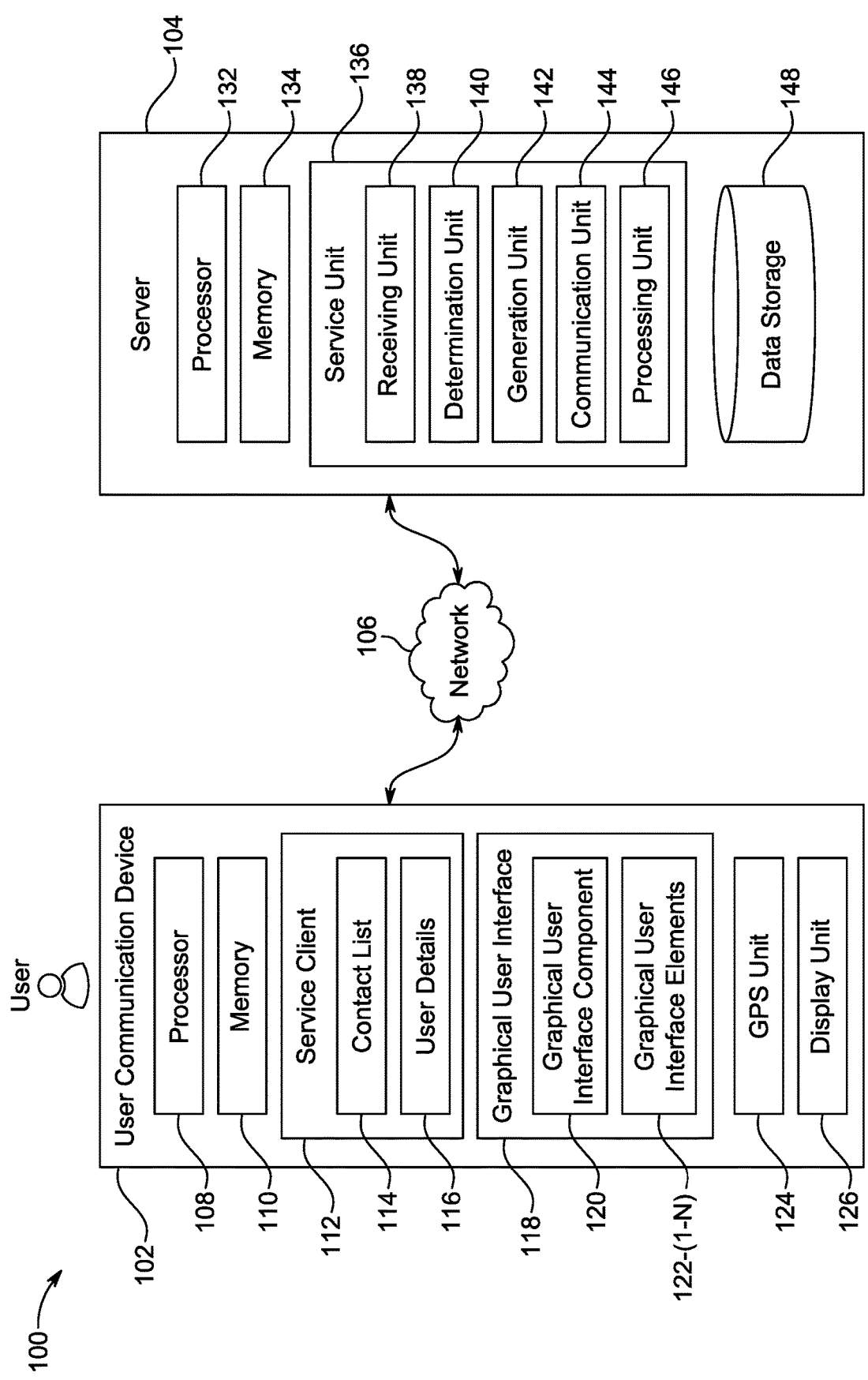
FIG. 1 depicts an implementation of an architecture of a system for customizing a healthcare service for a user, according to certain embodiments.

Various embodiments will hereinafter be described in accordance with the appended drawings, which are provided to illustrate and not to limit the scope of the disclosure in any manner, wherein similar designations denote similar elements, and in which:

FIG. 1 depicts an implementation of an architecture of a system 100 for customizing a healthcare service for a user, according to certain embodiments.

The system 100 (interchangeably referred to as an emergency communication and response system) may include a user communication device 102, a server 104, and a network 106 enabling communication between the system components for information exchange. Although one server i.e., server 104 is shown to be included in the system 100, in some implementations, the system 100 may include more than one server.

In some embodiments, the user communication device 102 may be any device used by a user. In an implementation, the user communication device 102 may be any computing device, such as, but not limited to, a mobile device, a smart phone, a wearable device, a tablet, a personal digital assistant, a laptop, or any other type and/or form of computing device that is capable of communication. In other embodiments, the computing device includes a memory and a processor coupled to the memory.

According to an implementation, the server 104 may be configured to provide healthcare services to users. The healthcare services may be defined to encompass mental healthcare, medical emergency healthcare, primary/secondary healthcare, and the like. In an implementation, the server 104 may be deployed and/or executed on any type and form of computing device, for example, a computer, network device, or appliance capable of communicating on any type and form of network (such as the network) and perform the operations described herein. In some embodiments, the server 104 may be implemented across a plurality of servers, thereby, tasks performed by the server 104 may be performed by the plurality of servers. These tasks may be allocated among the cluster of servers by an application, a service, a daemon, a routine, or other executable logic for task allocation. In an implementation, the server 104 may be owned or managed or otherwise associated with an emergency service provider or any entity authorized thereof.

According to an embodiment, the network 106 may be a private network or a public network. Further, the network 106 may be connected via wired and/or wireless links. Wired links may include Digital Subscriber Line (DSL), coaxial cable lines, or optical fiber lines. Wireless links may include Bluetooth®, Wi-Fi®, Worldwide Interoperability for Microwave Access (WiMAX®), an infrared channel or a satellite band. The wireless links may also include any cellular network standards to communicate among mobile devices. The network standards may qualify as one or more generations of mobile telecommunication standards by fulfilling a specification or standards such as the specifications maintained by the International Telecommunication Union. Examples of cellular network standards include Advanced Mobile Phone System (AMPS), Global System for Mobile (GSM), General Packet Radio Services (GPRS), Universal Mobile Telecommunications Service (UMTS), and Code-Division Multiple Access (CDMA). Wireless standards may use various channel access methods, e.g., Frequency-Division Multiple Access (FDMA), Time Division Multiple Access (TDMA), Code-Division Multiple Access (CDMA), or Spatial Division Multiple Access (SDMA). In some embodiments, different types of data may be transmitted via different links and standards. In other embodiments, the same types of data may be transmitted via different links and standards.

Further, the network 106 may be any type and/or form of network. The geographical scope of the network may vary widely and the network 106 may be a local-area network (LAN), e.g., Intranet, a wide area network (WAN), or the Internet. The network 106 may utilize different techniques and layers or stacks of protocols, including, e.g., the Ethernet protocol, and the internet protocol suite (TCP/IP). The TCP/IP internet protocol suite, may include application layer, transport layer, internet layer, or the link layer. The network 106 may be a type of broadcast network, a telecommunications network, a data communication network, or a computer network.

According to an implementation, the user communication device 102 may include a processor 108 and a memory 110. In an implementation, the processor 108 may be any logic circuitry that responds to and processes instructions fetched from the memory 110. In many embodiments, the processor 108 may be provided by a microprocessor unit, e.g., such as those manufactured by Intel Corporation of Mountain View, California; those manufactured by Motorola Corporation of Schaumburg, Illinois; the ARM processor or those manufactured by Advanced Micro Devices of Sunnyvale, California.

The memory 110 may include one or more memory chips capable of storing data and allowing any storage location to be directly accessed by the processor 108. The memory 110 may be Dynamic Random-Access Memory (DRAM) or any variants.

In an implementation, the user communication device 102 may further include a service client 112. The service client 112 may include a contact list 114, user details 116, and a graphical user interface (GUI) 118. The GUI 118 may include a GUI component 120 and one or more GUI elements 122-(1-N) (interchangeably referred to as contextual GUI elements 122-(1-N)). In some embodiments, the one or more GUI elements 122-(1-N) may be a single GUI element (all GUI elements of GUI elements 122-(1-N) are subsequently referred to as GUI element 122-1 but the description may be generalized to any of GUI elements 122-(1-N)). In examples, the contact list 114 may include contact details of healthcare professionals, hospitals, law enforcement offices, emergency contacts, and family contacts. In an example, the contact details may include email addresses and phone numbers (or contact numbers). Further, in examples, the user details 116 may include information of the user such as medical condition of the user, emergency contact details of the user, home address of the user, workplace details of the user, and nature of work of the user.

In an implementation, the contact list 114 and the user details 116 may be periodically or dynamically updated as required. In an example, the user may update the contact list 114 and the user details 116 while setting up the user communication device 102 or during a registration process of the user communication device 102.

In an implementation, the GUI 118 may be a keyboard, a mouse, a touch screen, a haptic sensor, a voice-based input unit, or any other appropriate user interface. Further, the GUI component 120 may be an emergency support request button or an emergency support request icon. In an example, when the user of the user communication device 102 requires medical assistance, the user may activate the GUI component 120 by pressing the GUI component 120 for a predetermined period of time. In an implementation, the user communication device 102 may be configured to transmit a communication signal (interchangeably referred to as communication) to the server 104 responsive to activation of the GUI component 120 via the network 106.

The one or more GUI elements 122-(1-N) (hereinafter collectively referred to as GUI elements 122-(1-N), and individually referred to as a GUI element 122), may include a link to make a call to a phone number, a link to send an SMS to the phone number, a link to send an email to a defined email address with a specified subject, and a link to a specified internet address. In examples, the phone number may be a contact information of at least one of a healthcare professional, a hospital, a law enforcement agency, emergency contact details and family contact. In an example, the links may be hyperlinks.

In an implementation, the server 104 may receive the communication signal from the user communication device 102 responsive to activation of the GUI component 120. The server 104 may generate the one or more GUI elements 122-(1-N) and communicate the one or more GUI elements 122-(1-N) to the user communication device 102.

According to an implementation, the user communication device 102 may include a global positioning system (GPS) unit 124. The GPS unit 124 may be configured to record a current location of the user communication device 102. In an example, the GPS unit 124 may periodically record the location of the user communication device 102. For example, the frequency of recording may be in the order of minutes, seconds, milliseconds, or some other time period. In other examples, the GPS unit 124 may record the location of the user communication device 102 at non-periodic time intervals or when the GUI component 120 is activated by the user. In some aspects of the present disclosure, the GPS unit 124 may store the GPS data (i.e., the location of the user communication device 102) in the memory 110 to be processed further, for example, by the server 104.

The manner in which the GPS unit 124 records the location of the user communication device 102 is not described in full within this disclosure for the sake of brevity. Also, other ways of estimation and recording of the location of the user communication device 102 are possible and whilst not explicitly discussed, are contemplated herein. In an example, device sensors such as accelerometer, gyroscope, magnetometer, and other such sensors may be used for the estimation of the location of the user communication device 102. Also, the user communication device 102 may use General Packet Radio Service (GPRS) as an alternative or in addition to GPS unit 124 to determine the location of the user communication device 102. In an example, both the GPS unit 124 and the GPRS may be used for accurate determination of the location of the user communication device 102. In some examples, in scenarios where the GPS unit 124-1 is not able to acquire a location (for example, due to obstacles in mountainous regions, buildings or lack of line of sight), the GPRS may be used for the location determination.

In an implementation, the user communication device 102 may also include a display unit 126, such as a screen, a monitor connected to the device in any manner, or any other appropriate display. In an implementation, the user communication device 102 may display received content (for example, GUI elements 122-(1-N)) for the user using the display unit 126 and is able to accept user interaction via GUI 118 responsive to the displayed content.

According to an implementation, the server 104 may include a processor 132 and a memory 134. In an implementation, the processor 132 may be any logic circuitry that responds to and processes instructions fetched from the memory 134. In many embodiments, the processor 132 may be provided by a microprocessor unit.

The memory 134 may include one or more memory chips capable of storing data and allowing any storage location to be directly accessed by the processor 132. The memory 134 may be Dynamic Random-Access Memory (DRAM) or any variants, including static Random-Access Memory (SRAM). In some embodiments, the memory 134 may be non-volatile. The memory 134 may be based on any of the above-described memory chips, or any other available memory chips capable of operating as described herein.

In an implementation, the server 104 may include a service unit 136. The service unit 136 may include a receiving unit 138, a determination unit 140, a generation unit 142, a communication unit 144, and a processing unit 146. In an implementation, the receiving unit 138, the determination unit 140, the communication unit 144, and the processing unit 146 may be coupled to the processor 132 and the memory 134. In some embodiments, the receiving unit 138, the determination unit 140, the generation unit 142, the communication unit 144, and the processing unit 146, amongst other units, may include routines, programs, objects, components, data structures, etc., which may perform particular tasks or implement particular abstract data types. The receiving unit 138, the determination unit 140, the generation unit 142, the communication unit 144, and the processing unit 146 may also be implemented as, signal processor(s), state machine(s), logic circuitries, and/or any other device or component that manipulates signals based on operational instructions.

In some embodiments, the receiving unit 138, the determination unit 140, the generation unit 142, the communication unit 144, and the processing unit 146 may be implemented in hardware, instructions executed by a processing unit, or by a combination thereof. The processing unit 146 may comprise a computer, a processor, a state machine, a logic array or any other suitable devices capable of processing instructions. The processing unit 146 may be a general-purpose processor that executes instructions to cause the general-purpose processor to perform the required tasks or the processing unit 146 may be dedicated to performing the required functions. In some embodiments, the receiving unit 138, the determination unit 140, the generation unit 142, the communication unit 144, and the processing unit 146 may be machine-readable instructions that, when executed by a processor/processing unit, perform any of desired functionalities. The machine-readable instructions may be stored on an electronic memory device, hard disk, optical disk or other machine-readable storage medium or non-transitory medium. In an implementation, the machine-readable instructions may also be downloaded to the storage medium via a network connection. In an example, machine-readable instructions may be stored in the memory 134.

In an implementation, the server 104 may include a data storage 148. The data storage 148 may store information associated with the user communication device 102 and the user of the user communication device 102. In examples, the server 104 may obtain the contact list 114 and the user details 116 from the user communication device 102 and store in the data storage 148. In an example, the information associated with the user communication device 102 and the user of the user communication device 102 stored in data storage 148 may be periodically or dynamically updated as required. In an implementation, data storage 148 may include any type or form of storage, such as a database or a file system or coupled to the memory 134.

According to an implementation, processing unit 146 of the server 104 may be configured to register the user communication device 102 with the server 104 based on assigning a unique identification (ID) number to the user communication device 102. In some implementations, the user of the user communication device 102 may be prompted to login to a particular website to register the user communication device 102 with the server 104. The user may be prompted to provide his or her country code and phone number to register the user communication device 102. Once the user provides his or her country code and phone number, the user communication device 102 is registered with the server 104. In an implementation, information about the registered user communication device 102 may be stored in the memory 134.

According to aspects of the present disclosure, a user in an emergency situation (for example, if a user is injured in a car accident, a user is feeling suicidal or a user is facing a crime scene) or even otherwise in a normal situation, the user may seek help using the user communication device 102. In an implementation, the user may interact with the GUI component 120 to activate the GUI component 120. In an example, the user may interact with the GUI component 120 by pressing the GUI component 120 for a predetermined period of time. In some implementations, the user may interact with the GUI component 120 by touching or tapping the GUI component 120 for a predetermined period of time. Responsive to the user interaction, the GUI component 120 may get activated. In an implementation, the user communication device 102 may be configured to transmit the communication signal to the server 104 responsive to the activation of the GUI component 120.

Figure 2:
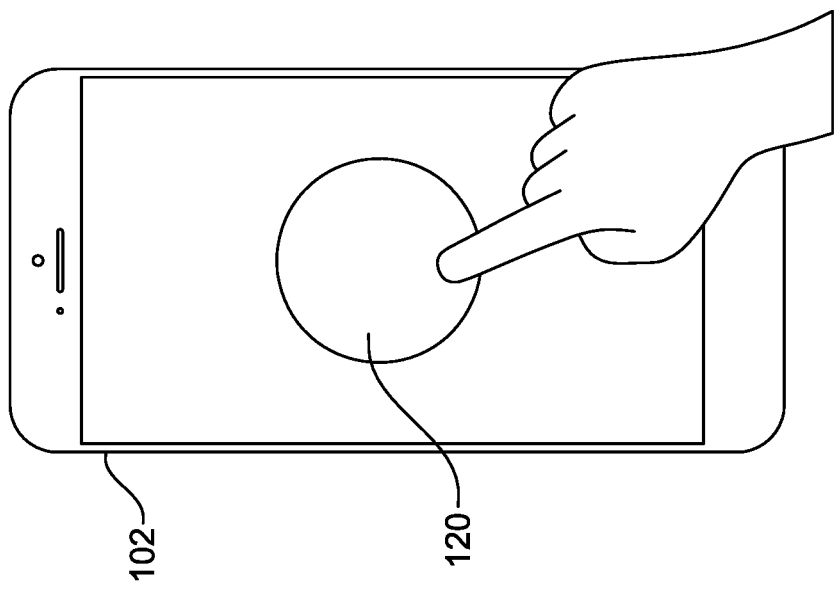
FIG. 2 depicts a user communication device comprising a graphical user interface (GUI) component, according to certain embodiments.

FIG. 2 depicts the user communication device 102 comprising the GUI component 120, according to certain embodiments. As shown in the example of FIG. 2, the user of the user communication device 102 interacts with the GUI component 120 using a finger. Although, it has been shown that the GUI component 120 is located at the front of the user communication device 102, in some embodiments, the GUI component 120 may be located at any location of the user communication device 102.

Referring back to FIG. 1, the receiving unit 138 may be configured to receive the communication signal from the user communication device 102 responsive to the activation of the GUI component 120. In an implementation, the determination unit 140 may be configured to determine date and time of activation of the GUI component 120 by the user. According to an implementation, the determination unit 140 may acquire information about the date and the time of activation of the GUI component 120 from the user communication device 102. In an implementation, the processor 108 of the user communication device 102 may be configured to determine the date and the time of activation of the GUI component 120. In an implementation, the determination unit 140 may be configured to obtain information of the user from the user communication device 102. In examples, the information of the user includes at least one of, medical condition of the user (including physical, mental, etc.), emergency contact details of the user, home address of the user, workplace details of the user, and nature of work of the user. In an example, the determination unit 140 may retrieve the information of the user from the data storage 148. In an implementation, the determination unit 140 may be configured to determine the current location of the user communication device 102.

According to an implementation, the determination unit 140 may determine, responsive to receiving the communication signal, contextual information based at least on the date and the time of activating the GUI component 120, the information of the user from the user communication device 102, the current location of the user communication device 102, and current health state of the user. The contextual information may be the date and the time of activating the GUI component 120, the information of the user associated with the user communication device 102, the current health state of the user (for example, mentally stressed, physically injured, etc.), and the current location of the user communication device 102. The current health state of the user may be determined, for example, based on information such as blood pressure, heartbeat rate, breathing rate, etc., obtained using wearable devices coupled to the user communication device 102. In some examples, digital features provided by the user communication device 102 such as crash detection may be used as the current heath state of the user. According to an implementation, the generation unit 142 may be configured to generate at least one contextual GUI element 122 using the contextual information. In an implementation, the generation unit 142 may be configured to generate the at least one contextual GUI element using at least one of a contact, a recipient, and an internet address that support the user contextually based on the at least on the date and time of activating the GUI component 120, the information of the user associated with the user communication device 102, and the current location of the user communication device 102.

In one or more examples, the at least one contextual GUI element 122 may include at least one of a link to make a call to a phone number, a link to send an SMS to the phone number, a link to send an email to a defined email address with a specified subject, and a link to a specified internet address. In another example, the phone number may be a contact number of at least one of a healthcare professional, a hospital, a law enforcement office, an emergency contact, and a family contact. In examples, each link may be an action-based link that triggers a specific action. In an example, the call may be an automated call that may be customized by the generation unit 142. Likewise, the SMS and the email may be customized by the generation unit 142.

In an implementation, the communication unit 144 may communicate the at least one contextual GUI element 122 to the user communication device 102. According to an implementation, the at least one contextual GUI element 122 is configured to execute a corresponding action when activated.

Figure 3:
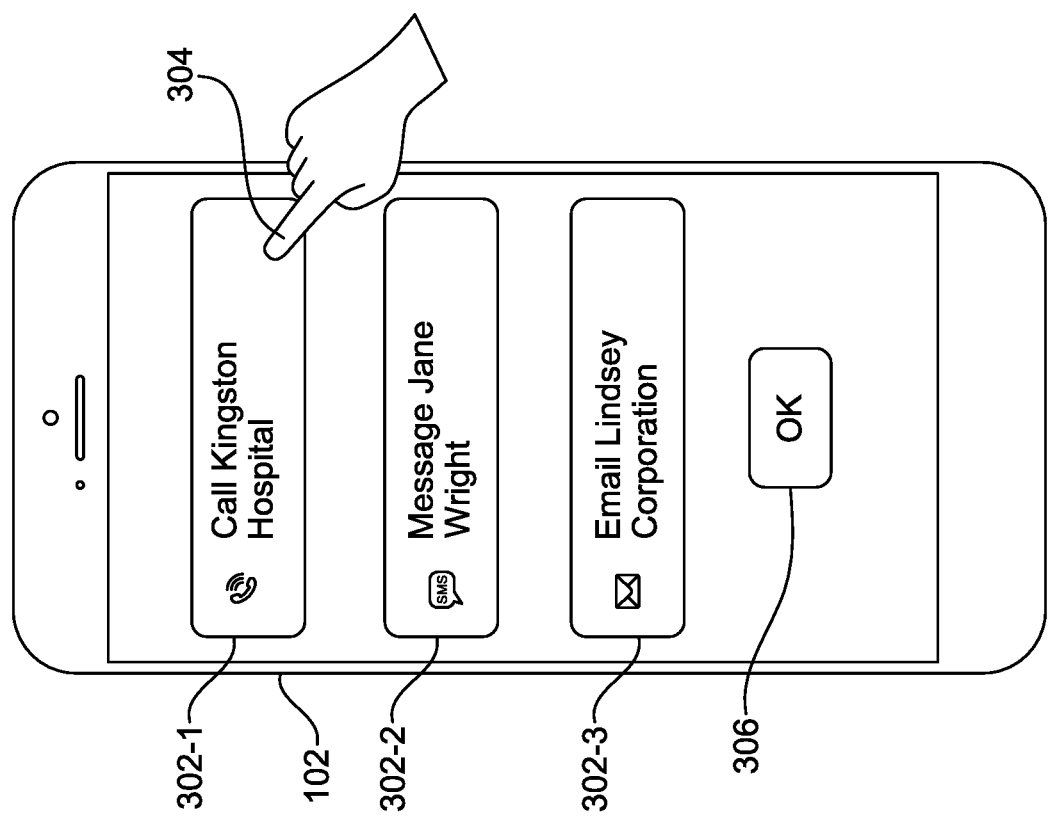
FIG. 3 depicts a plurality of GUI elements generated on the user communication device, according to certain embodiments.

FIG. 3 depicts a plurality of GUI elements generated on the user communication device 102, according to certain embodiments.

As described earlier, the server 104 may receive a communication signal from the user communication device 102 responsive to activation of the GUI component 120 on the user communication device 102. In response to receiving the communication signal from the user communication device 102, the server 104 may generate at least one contextual GUI element 122 and communicate the at least one contextual GUI element 122 to the user communication device 102. In an implementation, the at least one contextual GUI element 122 is configured to execute a corresponding action when activated.

In the example shown in FIG. 3, three contextual GUI elements are generated and communicated to the user communication device 102 based on health condition of the user. The three contextual GUI elements include "Call Kingston Hospital" 302-1, "Message Jane Wright" 302-2, and "Email Lindsey Corporation" 302-3. In an implementation, the contextual GUI element "Call Kingston Hospital" 302-1 may be a link to make a call to a phone number that belongs to the Kingston Hospital. In an example, the Kingston Hospital may be located nearby to the current location of the user communication device 102. Further, the contextual GUI element "Message Jane Wright" 302-2 may be a link to send an SMS to a phone number that belongs to Jane Wright. In an example, Jane Wright may be a relative (family) of the user of the user communication device 102. The contextual GUI element "Email Lindsey Corporation" 302-3 may be a link to send an email to an email address of Lindsey Corporation with a specified subject. In an example, Lindsey Corporation may be a workplace of the user of the user communication device 102. In examples, each link may be an action-based link that triggers a specific action.

In an implementation, after the three contextual GUI elements are displayed on the user communication device 102, the user may select at least one of the three contextual GUI elements according to his or her requirement. In examples, when the user selects at least one of the three contextual GUI elements, the selected contextual GUI elements get activated and a corresponding action is executed. In the example shown in FIG. 3, the user may select at least one of the three contextual GUI elements using a finger 304. After selecting at least one of the three contextual GUI elements using the finger 304, the user may click on OK icon 306. In an example, if the contextual GUI element "Call Kingston Hospital" 302-1 is selected, then a call may be made to the Kingston Hospital informing the hospital about medical assistance required by the user. In examples, the Kingston Hospital may be provided with the current location of the user communication device 102 of the user. This allows the user to be quickly transported to the Kingston Hospital.

In an example, if the contextual GUI element "Message Jane Wright" 302-2 is selected, then an SMS may be sent to Jane Wright informing Jane Wright that the user had a medical emergency and will be transported to the Kingston Hospital. In an example, if the contextual GUI element "Email Lindsey Corporation" 302-3 is selected, then an email may be sent to a human resource department of Lindsey Corporation informing Lindsey Corporation that the user had a medical emergency and is being transported to the Kingston Hospital.

While FIG. 3 shows generating links when using the GUI component 120 in response to the health condition, the server 104 is configured to generate appropriate contextual links in response to user mental condition such as user experiencing a stressful situation like facing a crime situation and the like.

Figure 4:
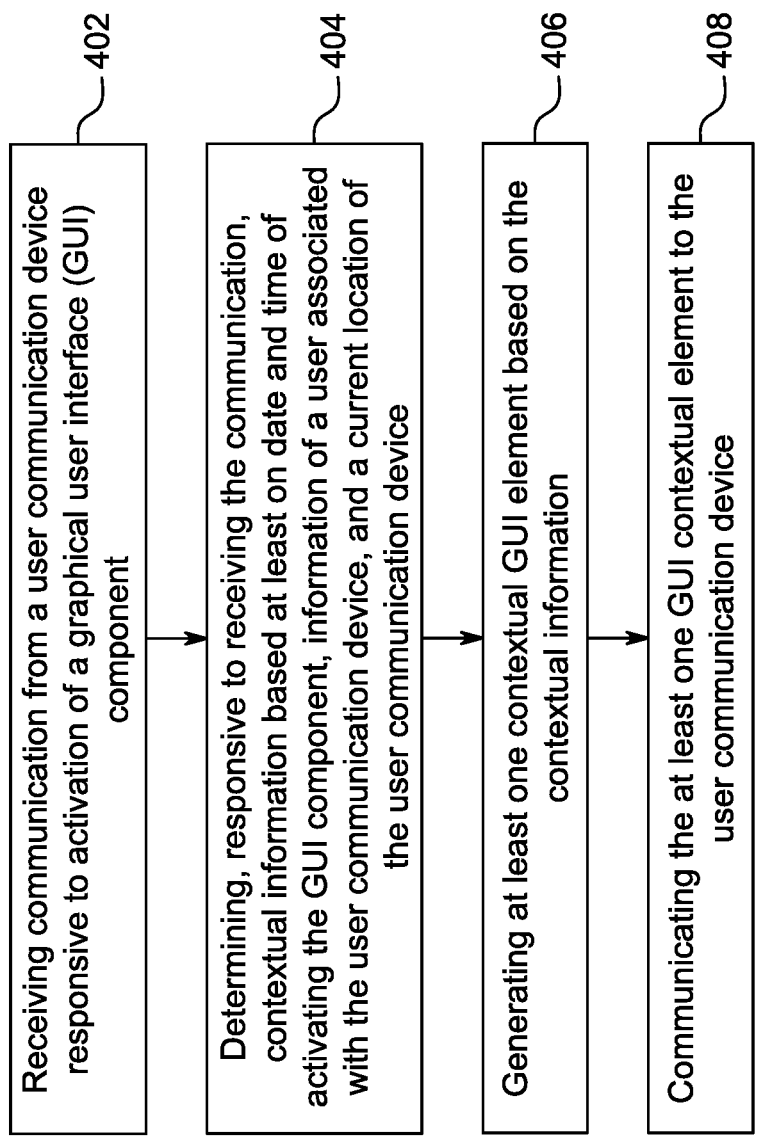
FIG. 4 illustrates a flowchart for generating one or more GUI elements based on contextual information, according to certain embodiments.

FIG. 4 illustrates a flowchart 400 for generating one or more graphical user interface (GUI) elements 122-(1-N) using contextual information, according to certain embodiments.

At step 402 of the flowchart 400, communication from the user communication device 102 may be received responsive to activation of the GUI component 120. In examples, the GUI component 120 may be an emergency support request button. According to an implementation, the receiving unit 138 may be configured to receive the communication from the user communication device 102 responsive to activation of the GUI component 120. In an implementation, the determination unit 140 may be configured to determine date and time of activation of the GUI component 120 by the user. The determination unit 140 may also be configured to obtain information of the user from the user communication device 102, and determine a location of the user communication device 102. In examples, the information of the user may include at least one of medical condition of the user, emergency contact details of the user, home address of the user, workplace details of the user, and nature of work of the user.

At step 404 of the flowchart 400, responsive to receiving the communication, contextual information may be determined based at least on the date and time of activating the GUI component 120, the information of the user associated with the user communication device 102, and the location of the user communication device 102. According to an implementation, the determination unit 140 may be configured to determine the contextual information based at least on the date and time of activating the GUI component 120, the information of the user associated with the user communication device 102, and the location of the user communication device 102.

At step 406 of the flowchart 400, at least one contextual GUI element 122-1 may be generated using the contextual information. According to an implementation, the generation unit 142 may be configured to generate the at least one contextual GUI element 122-1 using the contextual information. In examples, the at least one contextual GUI element 122-1 may include at least one of a link to make a call to a phone number, a link to send an SMS to the phone number, a link to send an email to a defined email address with a specified subject, and a link to a specified internet address. The phone number may be a contact number of at least one of a healthcare professional, a hospital, a law enforcement office, an emergency contact, and a family contact. According to an implementation, the generation unit 142 may be configured to generate the at least one contextual GUI element 122-1 based on processing at least one of a contact, a recipient, and an internet address that support the user contextually based on at least on the date and time of activating the GUI component 120, the information of the user associated with the user communication device 102, and the location of the user communication device 102.

At step 408 of the flowchart 400, the at least one GUI contextual element 122-1 may be communicated to the user communication device 102. According to an implementation, the communication unit 144 may be configured to communicate the at least one GUI contextual element 122-1 to the user communication device 102. In an implementation, the processing unit 146 may be configured to execute a corresponding action in response to user activation of the at least one contextual GUI element 122-1.

Obviously, numerous modifications and variations of the present disclosure are possible in light of the above teachings. It is therefore to be understood that within the scope of the appended claims, the invention may be practiced otherwise than as specifically described herein.

LIST OF ELEMENTS

100 System
102 User Communication Device
104 Server
106 Network
108 Processor
110 Memory
112 Service Client
114 Contact List
116 User Details
118 Graphical User Interface (GUI)
120 Graphical User Interface (GUI) Component
122 Graphical User Interface (GUI) Element
122-(1-N) Graphical User Interface (GUI) elements
122-1 GUI contextual element
124 Global Positioning System (GPS) Unit
126 Display Unit
132 Processor
134 Memory
136 Service Unit
138 Receiving Unit
140 Determination Unit
142 Generation Unit
144 Communication Unit
146 Processing Unit
148 Data Storage
302-1 "Call Kingston Hospital"
302-2 "Message Jane Wright"
302-3 "Email Lindsey Corporation"
304 Finger
306 OK Icon
400 Flowchart
402 Step
404 Step
406 Step
408 Step

What is claimed is:

1. A method for customizing a service, the method comprising:
receiving, by one or more servers, communication from a user communication device responsive to activation of a graphical user interface (GUI) component;
determining, responsive to receiving the communication, by the one or more servers, contextual information associated with the user, wherein the contextual information is information indicative of a current state of a user of the user communication device based at least on date and time of activating the GUI component, information of a user associated with the user communication device, and a location of the user communication device;
generating, by the one or more servers, at least one contextual GUI element based on the contextual information, wherein the at least one contextual GUI element is a communication option generated to assist the user in contacting a relevant support for the current state; and communicating, by the one or more servers, the at least one contextual GUI element to the user communication device.

2. The method as claimed in claim 1, further comprising executing a corresponding action in response to user activation of the at least one contextual GUI element, wherein the corresponding action comprises making a call, sending a message, sending an email and opening a predefined internet address.

3. The method as claimed in claim 1, wherein the at least one contextual GUI element comprises at least one of a link to make a call to a phone number, a link to send an SMS to the phone number, a link to send an email to a defined email address with a specified subject, and a link to a specified internet address, wherein the phone number is a contact number of at least one of a healthcare professional, a hospital, a law enforcement office, an emergency contact, and a family contact.

4. The method as claimed in claim 1, further comprising:
determining, by the one or more servers, the date and time of activation of the GUI component by the user based on at least date and time of activation from the user communication device;
obtaining, by the one or more servers, the information of the user from the user communication device; and
determining, by the one or more servers, the location of the user communication device based on the location captured by the user communication device when the GUI component is activated.

5. The method as claimed in claim 1, wherein generating the at least one contextual GUI element comprises:
processing, by the one or more servers, at least one of a contact, a recipient, and an internet address that supports the user contextually based on the at least date and time of activating the GUI component, the information of a user associated with the user communication device, and the location of the user communication device.

6. The method as claimed in claim 1, wherein the information of the user comprises at least one of medical condition of the user, emergency contact details of the user, home address of the user, workplace details of the user, and nature of work of the user.

7. The method as claimed in claim 1, wherein the GUI component is an emergency support request button.

8. A system comprising:
a user communication device configured to transmit communication responsive to activation of a graphical user interface (GUI) component;
one or more servers configured to:
receive the communication from the user communication device;
determine, responsive to receiving the communication, contextual information associated with the user, wherein the contextual information is information indicative of a current state of a user of the user communication device based at least on date and time of activating the GUI component, information of a user associated with the user communication device, and location of the user communication device;
generate, by the one or more servers, at least one contextual GUI element based on the contextual information, wherein the at least one contextual GUI element is a communication option generated to assist the user in contacting a relevant support for the current state; and
communicate the at least one contextual GUI element to the user communication device.

9. The system as claimed in claim 8, wherein the at least one contextual GUI element is configured to execute a corresponding action when activated, wherein the corresponding action comprises making a call, sending a message, sending an email and opening a predefined internet address.

10. The system as claimed in claim 8, wherein the at least one contextual GUI element comprises at least one of a link to make a call to a phone number, a link to send an SMS to the phone number, a link to send an email to a defined email address with a specified subject, and a link to a specified internet address, wherein the phone number is a contact information of at least one of a healthcare professional, a hospital, a law enforcement office, an emergency contact, and a family contact.

11. The system as claimed in claim 8, wherein the one or more servers are further configured to:
determine the date and time of activation of the GUI component by the user based at least on the date and time of activation from the user communication device;
obtain the information of the user from the user communication device; and
determine the location of the user communication device based on the location captured by the user communication device when the GUI component is activated.

12. The system as claimed in claim 8, wherein the one or more servers are configured to generate the at least one contextual GUI element using at least one of a contact, a recipient, and an internet address that supports the user contextually based on the at least date and time of activating the GUI component, the information of a user associated with the user communication device, and the location of the user communication device.

13. The system as claimed in claim 8, wherein the information of the user comprises at least one of medical condition of the user, emergency contact details of the user, home address of the user, workplace details of the user, and nature of work of the user.

14. The system as claimed in claim 8, wherein the GUI component is an emergency support request button.

15. A computer program product comprising instructions which, when the program is executed by a computing device having a memory and a processor coupled to the memory, causes the computing device to:
receive communication from a user communication device responsive to activation of a graphical user interface (GUI) component;
determine, responsive to receiving the communication, contextual information associated with the user, wherein the contextual information is information indicative of a current state of a user of the user communication device based at least on date and time of activating the GUI component, information of a user associated with the user communication device, and a location of the user communication device;
generate at least one contextual GUI element based on the contextual information, wherein the at least one contextual GUI element is a communication option generated to assist the user in contacting a relevant support for the current state; and
communicate the at least one contextual GUI element to the user communication device.

16. The computer program product as claimed in claim 15, wherein the computing device executes a corresponding action in response to the user activation of the at least one contextual GUI element, wherein the corresponding action comprises making a call, sending a message, sending an email and opening a link to a predefined internet address.

17. The computer program product as claimed in claim 15, wherein the at least one contextual GUI element comprises at least one of a link to make a call to a phone number, a link to send an SMS to the phone number, a link to send an email to a defined email address with a specified subject, and a link to a specified internet address, wherein the phone number is a contact number of at least one of a healthcare professional, a hospital, a law enforcement office, an emergency contact, and a family contact.

18. The computer program product as claimed in claim 15, wherein the computing device is configured to:
   determine the date and time of activation of the GUI component by the user, by acquiring the date and time of activation from the user communication device;
   obtain the information of the user from the user communication device; and
   determine the location of the user communication device based on a location captured by the user communication device when the GUI component is activated.

19. The computer program product as claimed in claim 15, wherein generating the at least one contextual GUI element comprises processing, by the one or more servers, at least one of a contact, a recipient, and an internet address that supports the user contextually based on the at least date and time of activating the GUI component, information of a user associated with the user communication device, and the current location of the user communication device.

20. The computer program product as claimed in claim 15, wherein the information of the user comprises at least one of medical condition of the user, emergency contact details of the user, home address of the user, workplace details of the user, and nature of work of the user.

* * * * *